United States Patent [19]

Epstein et al.

[11] 4,048,022

[45] Sept. 13, 1977

[54] SIMULANT COMPOUND AND METHOD FOR TESTING AN AGENT ALARM

[75] Inventors: Joseph Epstein; Lewis M. Berkowitz, both of Baltimore, Md.

[73] Assignee: The United States of America as represented by the Secretary of the Army, Washington, D.C.

[21] Appl. No.: 702,371

[22] Filed: July 2, 1976

[51] Int. Cl.² .................... G01N 27/46; G01N 27/50
[52] U.S. Cl. ..................................... 204/1 T; 252/408
[58] Field of Search .............. 204/1 T, 1 B, 1 N, 1 K; 252/408 R

[56] References Cited

U.S. PATENT DOCUMENTS

| 3,844,905 | 10/1974 | Epstein et al. | 204/1 T |
| 3,972,783 | 8/1976 | Poziomek et al. | 204/1 T |

Primary Examiner—G. L. Kaplan

Attorney, Agent, or Firm—Nathan Edelberg; Kenneth P. Van Wyck

[57] ABSTRACT

A method of challenging an agent alarm for the detection of V and G agents through the use of a simulant compound which has no significant toxicity and which will test the three principal components of the alarm, namely the conversion filler, heating element, and the detection cell. The stimulant compound has the general formula $$R'-O-\underset{\underset{CH_3}{|}}{\overset{\overset{O}{\|}}{P}}-S-R''$$

wherein R'' is a lower alkyl group selected to produce a readily displaced alkylmercapto moiety when reacted with the AgNO₃ and KF of the conversion filter and R is a longer chain alkyl selected to give a volatility similar to that of less volatile G agents.

5 Claims, No Drawings

SIMULANT COMPOUND AND METHOD FOR TESTING AN AGENT ALARM

DEDICATORY CLAUSE

The invention described herein may be manufactured, used, and licensed by or for the Government for governmental purposes without the payment to us of any royalty thereon.

DESCRIPTION OF THE INVENTION

Our invention relates to a method of challenging a V and G toxic agent alarm as disclosed in U.S. Patent Application, Ser. No. 768,560 filed on Oct. 16, 1968 now U.S. Pat. No. 3,957,611, through use of a simulant compound of no significant toxicity.

The toxic agent alarm disclosed in U.S. Patent Application, Ser. No. 768,560 was developed to monitor the atmosphere around industrial plants and on the battlefield for the presence of low concentrations of toxic compounds such as hydrogen cyanide, hydrogen sulfide, and chemical warfare agents of the class known as V and G agents. The development of the above monitoring device has consequently brought forth the problem of testing the functional reliability and sensitivity of the alarm without resorting to the use of the inherently dangerous toxic agents themselves. The problem has been confronted by developing simulant compounds that have no significant toxicity and which would nevertheless mimic toxic G class agents under anticipated operating conditions, such as disclosed in U.S. Pat. Nos. 2,926,072 and 2,929,791, and in U.S. Patent Application, Ser. No. 513,016, filed Oct. 8, 1974, now U.S. Pat. No. 3,972,783.

The simulant materials developed, disclosed above, have adequately mimicked G agents, particularly the later simulants $H_3C-SO_2Fl$, but have not been useful in challenging the agent alarm for V agents through means of testing the conversion filter and heating element of the alarm by which V agents are converted to their G analogues for detection by the electrode cell.

Benzene sulfonyl chloride (BSC) has found use as a test material for testing the proper operation of the agent alarm in the field. The properties of benzene sulfonyl chloride are such that only the heater element and detection cell of the alarm are placed under test, but the suitability of the conversion filter to convert V agents to fluoridates is left unchallenged. Thus, it is possible that the alarm could show a satisfactory response using benzene sulfonyl chloride and yet would not alarm when challenged by physiologically significant concentrations of the V agent.

A primary object of our invention is to provide a method whereby a toxic V and G agent alarm can be challenged by a compound which has no significant physiological activity, but which mimics the reactivity of V agents with the conversion filter, heating element and detection cell of the alarm to thus insure reliability of function and sensitivity of the alarm under anticipated operating conditions.

Other objects of our invention will be apparent from the specification as set forth below.

The standardized V and G agent electrical cell alarm and method disclosed in U.S. Patent Application, Ser. No. 768,560 is based upon the capability of the silver electrode to detect submicrogram quantities of cyanide ions. G agents are absorbed into a cell electrolyte and are directly reacted with an oxime, resulting in the rapid generation of cyanide ions. The cyanide ions, in turn, diffuse throughout the electrolyte and are detected by the silver electrode. V agents are not detected directly by the oxime reaction, but they are converted to the corresponding G analogues by means of a chemical reaction with an impregnate in a conversion prefilter. The G agents and analogues react with an oxime; i.e., isonitrosobenzoyl acetone (IBA) to liberate cyanide ions and subsequently produce the electrochemical reaction:

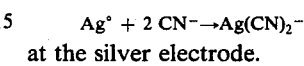

at the silver electrode.

Each decade change in cyanide concentration in the alarm cell electrolyte produces a 120 MV change in potential, enabling G and V agent detection and quantitative estimation. The mechanics of the oxime reaction are as follows:

1. Formation of the oxime anion

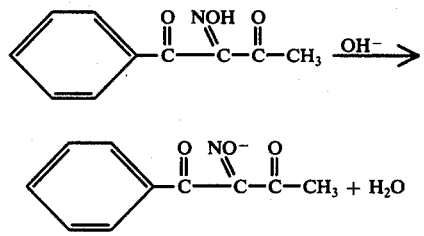

2. O-phosphorylation of the oxime anion

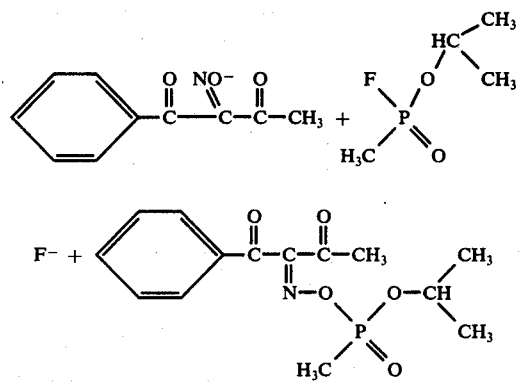

3. Rapid cleavage of the oxime phosphonate

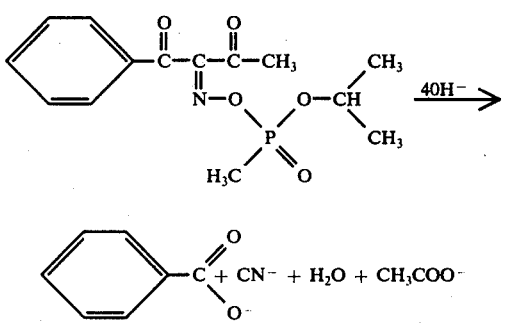

$$+\left[H_3C-P\begin{array}{c}O\\\diagup\\\diagdown\\O\end{array}\begin{array}{c}\\\\O-CH\end{array}\begin{array}{c}CH_3\\\\CH_3\end{array}\right]$$

Silver nitrate and potassium fluoridate are impregnated in the conversion filter to convert V agents to their G analogues, such as phosphonofluoridates, to react with the oxime; G agents being nonreactive with the chemical conversion filter composition. While not a part of this invention, U.S. Patent Application, Ser. No. 768,560 also disclosed the process of impregnating the conversion filter.

The problem of providing a simulant for V and G agents in testing of the agent alarm requires a simulant compound that has a volatility of the desired level to satisfy the specifications of the alarm system for G agents, (2) a level of volatility of the less volatile G agents such as GA, GD, GF and the like so as to test the function of the alarm heating element and (3) a reactivity with the alarm conversion filter to give a G agent simulant when challenging the detection cell of the alarm.

Applicants have discovered that compounds of the following formula (I):

$$R'-O-\underset{\underset{CH_3}{|}}{\overset{\overset{O}{\|}}{P}}-S-R''\quad (I)$$

wherein R' and R'' are alkyl groups and R'' is particularly chosen so that the alkylmercapto moiety is readily converted by the conversion filter into the corresponding fluoro compound (II); e.g. an alkyl of 5 – 7 carbons $$R'-O-\underset{\underset{CH_3}{|}}{\overset{\overset{O}{\|}}{P}}-Fl\quad (II)$$

and R' is a lower alkyl group chosen so that the resulting conversion fluoro compound has a volatility approximating that of benzene sulfonyl chloride; are effective simulants for V agents and their G analogues in challenging the conversion filter, heating element and detection cell of the agent alarm.

In particular, O-n-hexyl, S-ethyl methyl phosphonothiolate (III):

$$n-C_6H_{13}-O-\underset{\underset{CH_3}{|}}{\overset{\overset{O}{\|}}{P}}-S-C_2H_5\quad (III)$$

has been found to be an effective simulant compound for testing the alarm conversion filter and fluoro conversion product with a volatility approximating that of BSC for challenging the heating element and detection cell of the alarm. The compounds O-n-amyl, S-ethyl methylphosphonothiolate and O-n-heptyl S-ethyl phosphonothiolate can also be used as simulants in the instant invention.

The preferred simulant compound O-hexyl S-ethyl methylphosphonothiolate is synthesized in accordance with the following two step reaction equation:

$$C_2H_5-O-\underset{\underset{CH_3}{|}}{\overset{\overset{O}{\|}}{P}}-H\quad\xrightarrow{\underset{Na\ (trace)}{C_6H_{13}-OH}}$$

$$C_6H_{13}-O-\underset{\underset{CH_3}{|}}{\overset{\overset{O}{\|}}{P}}-H\quad\xrightarrow{\begin{array}{l}(1)\ NaOC_6H_{13}\\(2)\ S\\(3)\ C_2H_5Br\end{array}}$$

$$C_6H_{13}-O-\underset{\underset{CH_3}{|}}{\overset{\overset{O}{\|}}{P}}-S-C_2H_5$$

Preparation of O-hexyl S-ethyl methylphosphonothiolate

A mixture of 20.4 gms. (0.2 mole) n-hexyl alcohol, 21.6 gms. (0.2 mole) ethylmethylphosphinate and 0.2 gms. (0.01 mole) sodium was heated in a 170° bath under a 10cm. Vigreaux column and a total condensation partial takeoff still head. After approximately 4 ml. ethanol distilled off at 78°, the head temperature fell to ambient temperature. The reaction mixture was distilled at 15 mm. After a forerun below 95°, the main fraction distilled at 120° – 125° (the literature value is 117° – 119°/12 mm). The yield of n-hexyl methylphosphinate was 17.3 gm (0.106 mole; 53% of theory). The n-hexyl methylphosphinate in 12.5 ml n-hexyl alcohol was added to a solution of 2.43 gm (0.106 mole) sodium in 62.5 ml n-hexyl alcohol. The clear solution was stirred at ambient temperature for one hour. Sulfur (3.4 gm - 0.106 mole) was added in portions with stirring during 1 hour followed by a further 18 hours stirring at ambient temperature. By this time, almost all of the sulfur had disappeared. Ethyl bromide (11.6 gm-0.106 mole) was added in one portion and the reaction mixture was heated at 45° for 6 hours. Residual sulfur was filtered off, 100 ml water was added and the mixture was then extracted with benzene and dried over magnesium sulfate. After removal of the lower boiling materials, the main fraction was distilled at 98° – 103° at 0.7 mm to yield 10.9 gms (45% of theory) O-hexyl S-ethyl methylphosphonothiolate. The infra-red spectrum was consistent with the proposed structure and the elemental analysis was satisfactory (calculated: C, 48.1; H, 9.4; P, 13.8; S, 14.3 - Found: C, 48.8; H, 9.2; P, 13.8; S, 13.7).

EXAMPLE I

The V and G agent alarm responds to a concentration of GB agent in air of 0.2 μg/l (21 mv cell response within 2 minutes). When an amount of O-hexyl S-ethyl phosphonodithiolate in diethyl phthalate solution equivalent to 0.2 μg/liter GB in air was placed on the alarm filter, the alarm responded. The 0.2 μg/l GB level above is equivalent to 0.4 μg GB sampled by the alarm within 2 minutes at the rate of 1.0 liter per minute.

EXAMPLE II

The test was repeated as in Example I with the only change being that the conversion prefilter was removed and the O-hexyl S-ethyl phosphonothiolate was introduced directly to the detector cell. The alarm failed to respond.

The above examples demonstrate the effectiveness of the simulant compound in mimicking the toxic V agents and their corresponding conversion G analogues. The tests further illustrate that the instant invention challenges the alarm essential components, namely the conversion prefilter ability to convert the "agent" to a corresonding fluoro compound which is in turn used to challenge the detection cell for G agents and analogues.

The amount of simulant used in the method of this invention is not critical in itself provided that it be equivalent in concentration to 0.2 µg/l of GB agent in air. As experimentally determined, the simulant compound should be present in the preparation of approximately 1.2 times more simulant than G agent to effect an equivalent cell response (e.g. ≧0.5 µg/2.0 liter of air sampled by the alarm within 2 min.).

Applicants having disclosed their invention, obvious modification of the instant invention will be apparent to those skilled in the related chemical art and applicants thus desire to be limited only by the scope of the appended claims.

We claim:

1. A method of challenging a toxic V and G agent alarm so as to test the function and sensitivity of the alarm's conversion prefilter, heating element, and detection cell by using a simulant compound which has no significant toxicity, said alarm including an electrochemical cell with a silver electrode for the detection of CN$^-$ ions, said cell having an electrolyte including an oxime for reaction with phosphonofluoridates, G agents and analogues thereof, whereby CN$^-$ ions are generated, said alarm further including a conversion prefilter impregnated with AgNO$_3$ and KF for the conversion of V agents to their G analogues and a heating element for volatilizing the V agents, comprising the steps of providing an air sample containing said simulant compound having the formula $$R'-O-\underset{\underset{CH_3}{|}}{\overset{\overset{O}{\|}}{P}}-S-R''$$

wherein R" is a lower alkyl group selected to produce a readily displaced alkylmercapto moiety when reacted with the AgNO$_3$ and KF of the conversion filter and R' is a longer chain alkyl group selected to give a volatility similar to that of the less volatile G agents, reacting said simulant compound with the AgNO$_3$ and KF of the conversion filter to produce the corresponding fluoridate, heating the resulting fluoridate by means of the alarm heating element to volatilize the fluoridate, passing the volatilized fluoridate to the electrochemical detection cell and reacting said fluoridate with the oxime of the cell electrolyte to produce CN$^-$ ions, reacting the CN$^-$ ions at the silver electrode of the cell to produce a change in potential and monitoring the change in potential to determine the alarm challenge.

2. The method of claim 1 wherein R" is an ethyl group.

3. The method of claim 2 wherein R' is an alkyl of five to seven carbons.

4. The method of claim 3 wherein the simulant compound is O-n-hexyl, S-ethyl methylphosphonothiolate.

5. The method of claim 1 wherein the simulant is present in a concentration equivalent to 0.2 µg. GB agent/liter of air.

* * * * *